(12) United States Patent
Kyle

(10) Patent No.: US 7,608,097 B2
(45) Date of Patent: Oct. 27, 2009

(54) BONE SCREW WITH FLUID DELIVERY STRUCTURE

(75) Inventor: Richard F. Kyle, Long Lake, MN (US)

(73) Assignee: Millennium Medical Technologies, Santa Fe, NM (US)

( * ) Notice: Subject to any disclaimer, the term of this patent is extended or adjusted under 35 U.S.C. 154(b) by 842 days.

(21) Appl. No.: 10/836,006

(22) Filed: Apr. 29, 2004

(65) Prior Publication Data

US 2004/0267265 A1 Dec. 30, 2004

Related U.S. Application Data

(60) Provisional application No. 60/466,487, filed on Apr. 29, 2003.

(51) Int. Cl.
*A61B 17/86* (2006.01)
(52) U.S. Cl. .................................. 606/304; 606/93
(58) Field of Classification Search .............. 606/65, 606/69–73, 92–94, 300–321; 604/264, 523–539, 604/284
See application file for complete search history.

(56) References Cited

U.S. PATENT DOCUMENTS

| | | | |
|---|---|---|---|
| 2,570,465 A | 10/1951 | Lundholm | |
| 2,631,584 A | 3/1953 | Purificato | |
| 2,801,631 A | 8/1957 | Charnley | |
| 2,834,342 A | 5/1958 | Yost | |
| 3,051,169 A | 8/1962 | Grath | |
| 4,175,555 A | 11/1979 | Herbert | |
| 4,456,005 A | 6/1984 | Lichty | |
| 4,653,489 A | 3/1987 | Tronzo | |
| 4,760,844 A * | 8/1988 | Kyle | 606/65 |
| RE33,348 E | 9/1990 | Lower | |
| 5,019,079 A | 5/1991 | Ross | |
| 5,047,030 A | 9/1991 | Draenert | |
| 5,098,435 A | 3/1992 | Stednitz et al. | |
| 5,192,282 A | 3/1993 | Draenert | |
| 5,203,770 A * | 4/1993 | Wigness et al. | 604/506 |
| 5,279,567 A * | 1/1994 | Ciaglia et al. | 604/117 |
| 5,334,204 A | 8/1994 | Clewett et al. | |
| 5,484,442 A * | 1/1996 | Melker et al. | 606/79 |
| 5,514,137 A * | 5/1996 | Coutts | 606/62 |
| 5,735,898 A | 4/1998 | Branemark | |
| 5,743,912 A | 4/1998 | Lahille et al. | |
| 6,015,937 A * | 1/2000 | Branemark | 606/65 |
| 6,048,343 A | 4/2000 | Mathis et al. | |
| 6,210,376 B1 | 4/2001 | Grayson | |
| 6,214,012 B1 | 4/2001 | Karpman et al. | |
| 6,554,830 B1 * | 4/2003 | Chappius | 606/61 |
| 6,755,835 B2 * | 6/2004 | Schultheiss et al. | 606/73 |
| 2001/0021852 A1 | 9/2001 | Chappius | |

* cited by examiner

*Primary Examiner*—Thomas C Barrett
*Assistant Examiner*—Michael J Araj
(74) *Attorney, Agent, or Firm*—Kagan Binder, PLLC

(57) ABSTRACT

A device and method to mechanically strengthen bone matrix and deliver tissue reinforcement material to weakened areas in skeletal structures. A preferred embodiment is an orthopedic screw configured to receive and directionally disperse a therapeutic fluid through the screw's channels and apertures.

20 Claims, 5 Drawing Sheets

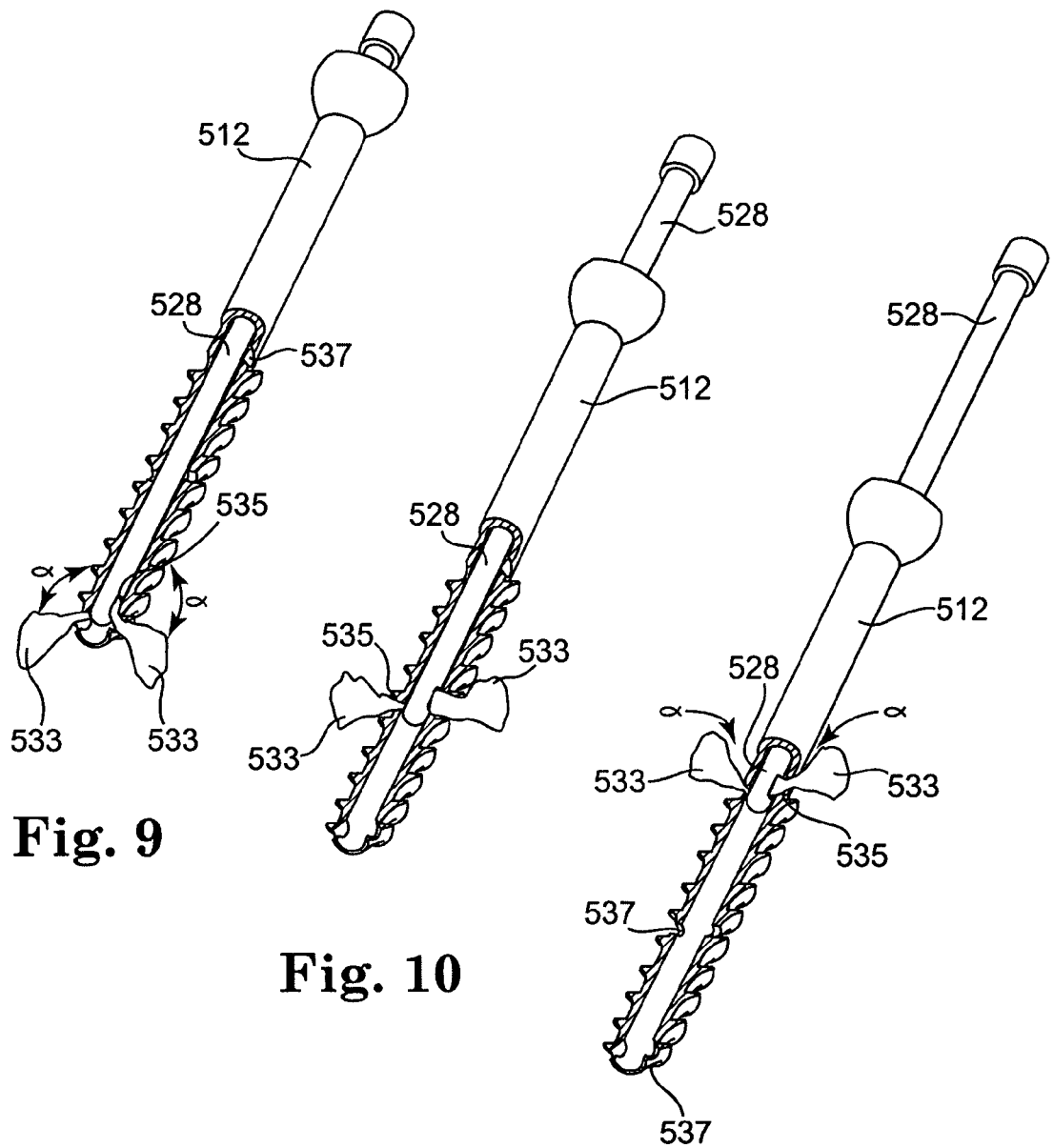

BONE SCREW WITH FLUID DELIVERY STRUCTURE

PRIORITY

Figures 1, 17:
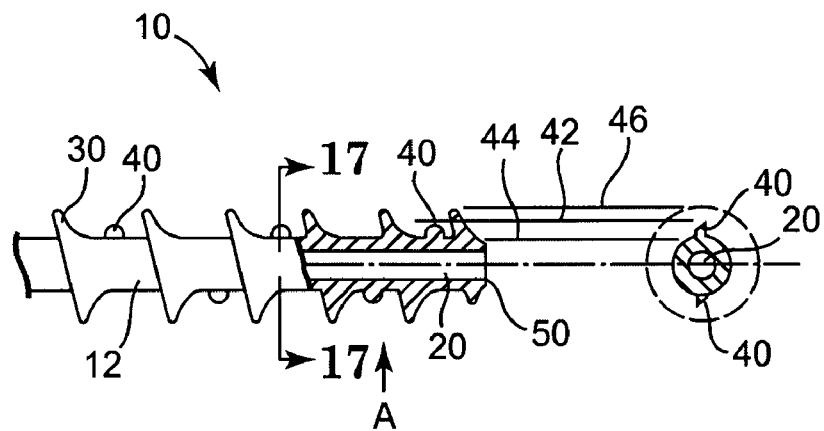

This application claims priority to Provisional Application No. 60/466,487 filed Apr. 29, 2003.

FIELD OF THE INVENTION

The invention relates to orthopedic devices used to reinforce bones in mammals.

BACKGROUND OF INVENTION

In any number of medical procedures it becomes necessary to deliver therapeutic material to an anatomic location. For example, it can be desirable to deliver materials usually as a fluid to particular locations within bone. This is particularly desirable when using bone screws. Materials such as calcium phosphate, hydroxyapatite, etc. are often needed to be delivered to aid in the fixation applied by an orthopedic screw.

Within the context of the present invention, which will be discussed in greater detail below, the inventors have discovered a method and apparatus which offer advantages over the currently known techniques. For convenience of explanation, the present invention will be described in conjunction with various applications, but principally bone screw and therapeutic material delivery systems. Various other applications and embodiments will be apparent in view of the following disclosure.

In the context of bone screws, bone screws may be applied to bone matrix for any number of reasons but usually such devices are attached for the purposes of repair of a weakened bone matrix in order to support bone or bone structure which has become fractured or weakened. In many cases, the fracturing of bone is in whole or in part due to disease. The bone breaks or weakens as a result of disease, for example, osteoporosis. Current techniques do not usually take into consideration that condition in the context of repair. The technique often used to repair bone may fail to address the situation under which the bone was fractured in the first place.

For example, in accordance with the conventional methods of attaching bone screws to bone, bone cement is injected through a pilot hole drilled into the bone prior to inserting the bone screw. After the bone screw is inserted into the site, the bone site theoretically hardens to strengthen the fixation site. This method lacks control over the location and the amount of bone cement applied. Often, difficulty in controlling the placement of a bone adhesive near tissues, specifically in the spinal cord region, allows improper placement resulting in injury. Too little bone cement or improper placement of the bone cement may result in a weak fixation site, which may lead to an undesirable extraction of the bone screw from the fixation site. For example, if the bone has been broken because of a chronic medical condition the use of cement in this fashion will not materially enhance fixation. Specifically, if the bone is weakened due to osteoporosis, then merely adding adhesive to the area may not necessarily address the pre-existing condition.

SUMMARY OF THE INVENTION

A device for entering an area of a host's bone matrix to mechanically strengthen the matrix and deliver tissue reinforcement material comprising; a shaft with a first external threaded portion, said shaft having a distal end, a middle portion and a proximal end; said shaft's proximal end configured to receive a fluid supply of tissue reinforcement material within walls of said shaft forming a lumen extending therethrough; walls forming at least one channel extending directionally from said lumen to at least one aperture formed by shaft walls to an outer surface of said device; and a sleeve sized to fit inside said lumen to selectively guide delivery of tissue reinforcement material.

BRIEF DESCRIPTION OF THE INVENTION

Figure 2:
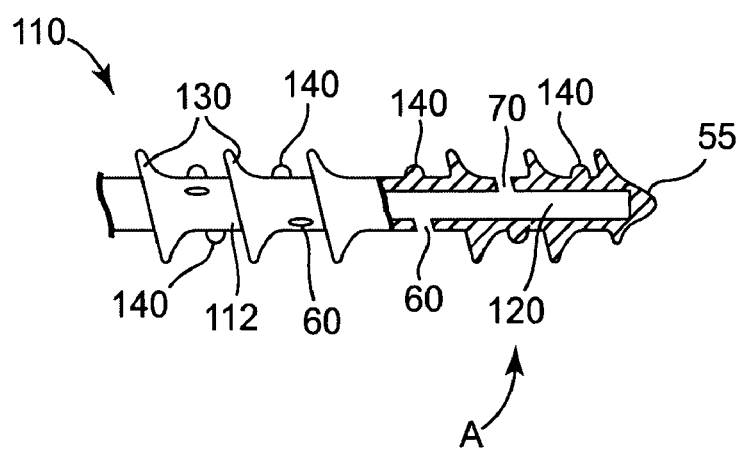
Figure 3:
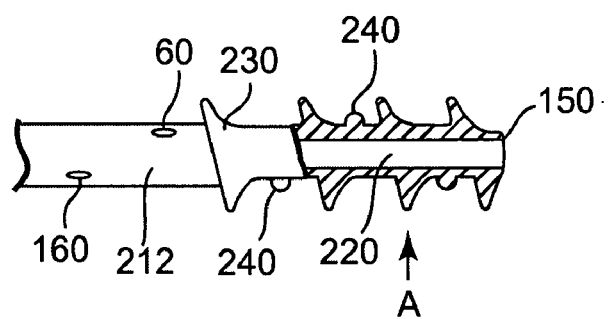
Figure 4:
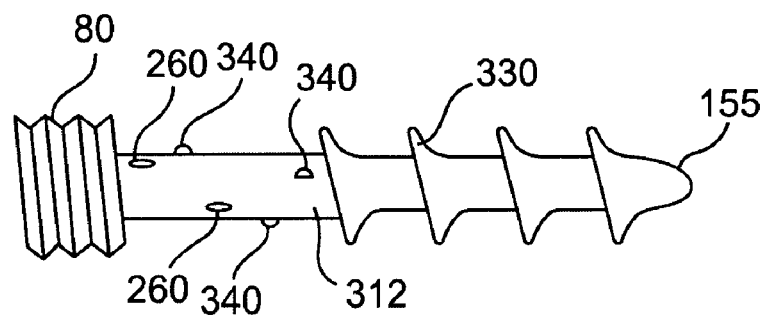
Figure 5:
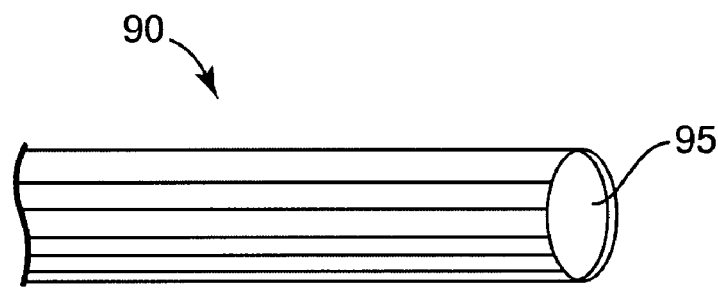
Figure 6:
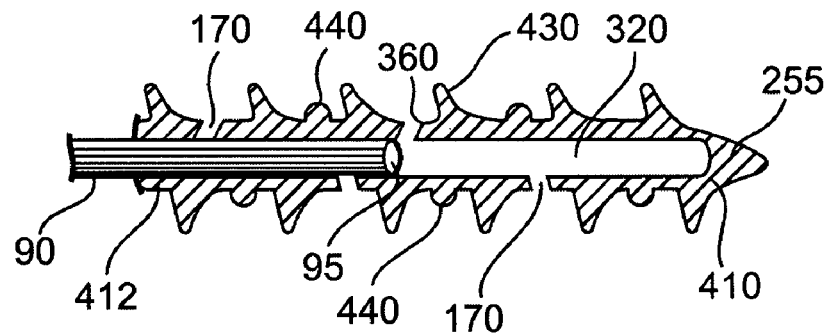
Figure 7:
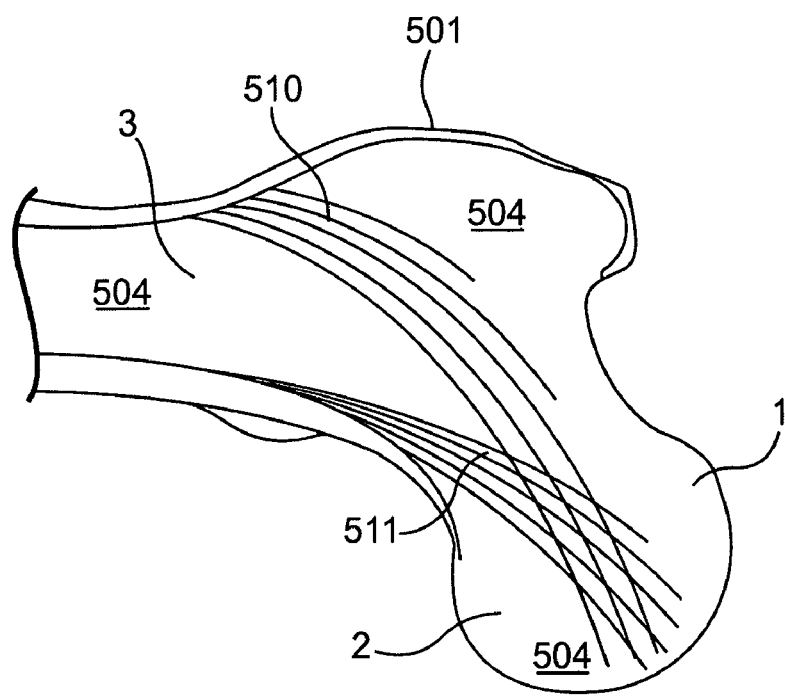
Figure 8:
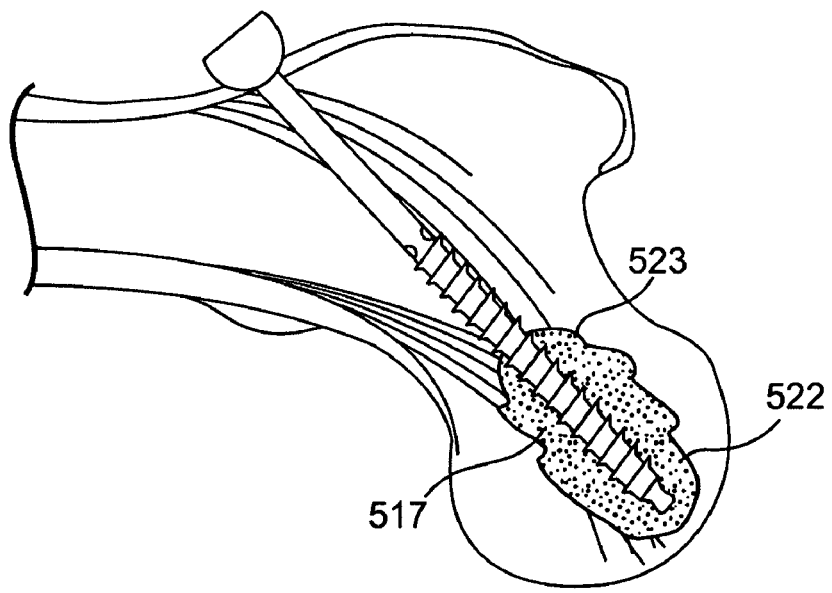
Figure 12:
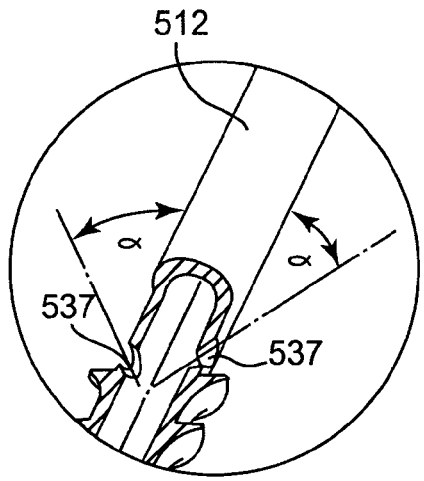
Figures 13, 14, 15:
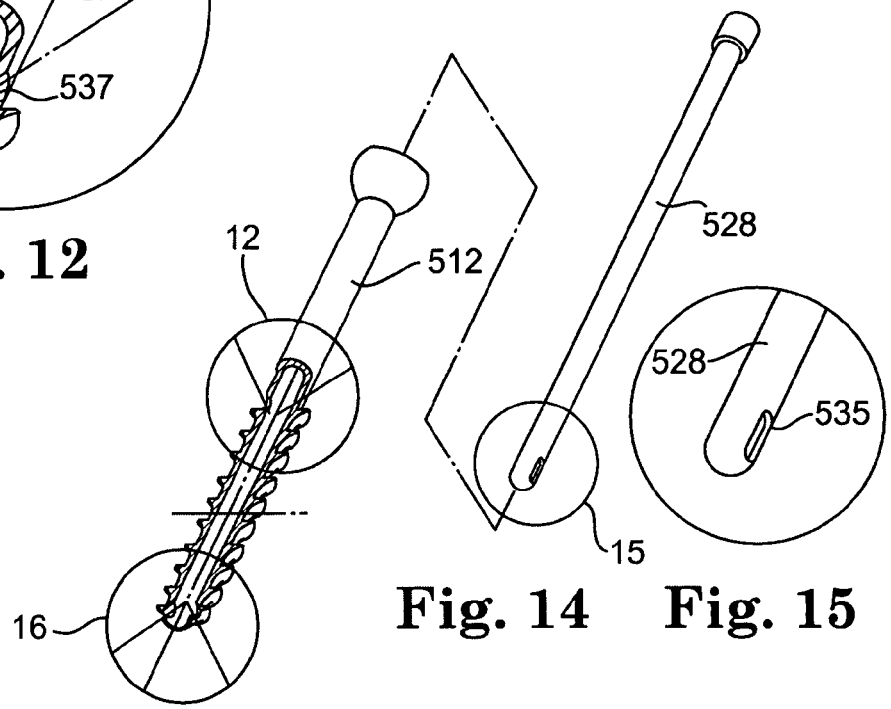
Figure 16:
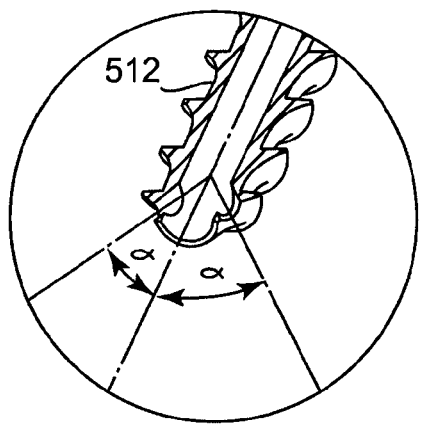

FIG. 1 is side and cutaway view of one embodiment.
FIG. 2 is a side and cutaway view of another embodiment.
FIG. 3 is a side and cutaway view of a third embodiment.
FIG. 4 is a side view of a fourth embodiment.
FIG. 5 is a side view of a sleeve.
FIG. 6 is a cutaway view illustrating insertion of a sleeve and enlargement of that sleeve.
FIG. 7 is a schematic body portion showing bone zones and trabeculae.
FIG. 8 is a view of FIG. 7 with a bone screw and bone reinforcing material optimally placed.
FIG. 9 is a partial cutaway view of one embodiment of a bone screw assembly deploying bone reinforcing material.
FIG. 10 is a partial cutaway view of one embodiment of a bone screw assembly deploying bone reinforcing material.
FIG. 11 is a partial cutaway view of one embodiment of a bone screw assembly deploying bone reinforcing material.
FIG. 12 is a partial cutaway view of angled proximal apertures.
FIG. 13 is a partial cutaway view of one embodiment of a bone screw assembly.
FIG. 14 is a view of one embodiment of a sleeve.
FIG. 15 is an expanded view of a portion of the sleeve of FIG. 14.
FIG. 16 is a partial cutaway view of angled distal apertures.
FIG. 17 is a section view of FIG. 1 along lines 17-17.

DETAILED DESCRIPTION OF THE INVENTION

In general, the present invention provides a device and method that enhances delivery of a reinforcement material to improve fixation without deleteriously affecting the performance of the device. The material applied to a weakened bone matrix would be more useful if it enhanced the fundamental integrity of the bone. Delivering calcium phosphate, hydroxyapatite, bone growth factors, or similarly functioning materials would strengthen the fundamental structure of the bone matrix. Controlled delivery of the therapeutic fluid as to location, rate, and dispersion of equally effective amounts would be of benefit to the patient. This could be achieved by carving a larger chamber slightly beyond that created by an orthopedic screw giving better access for the fluid into the bone matrix. Apertures along the screw shaft would also allow more fluid dispersion between screw and bone matrix, particularly where such apertures are angled to deliver fluid so that distal or proximal motion of the screw is specifically minimized and controlled.

A sleeve positioned within a central lumen of a screw would also control the fluid delivery to external apertures thereby achieving a more precise application. Furthermore, to decrease application pressure inherent in pushing fluid through a channel, the lumen and the channels connecting to outside apertures could be coated with a material to decrease friction between fluid and walls formed by such a screw.

Various bone screw configurations are known. For example, cannulated screws are known and typically used for conventional applications. Alternatively, such cannulated screws are utilized in connection with various techniques. For example, U.S. Pat. No. 6,214,012, issued 10 Apr. 2001, teaches a bone screw with apertures for delivery of bone cement or other medicaments to allow reinforcement of the surrounding bone. This patent also discloses a special adaptor at the head of the screw in order to make a connection for delivery of the cement or medications. However, such device does not enable the therapeutic fluid delivery with through-enlarging of a chamber in the bone matrix, selection of exterior apertures on a screw, precise delivery of material using specially angled apertures, or controlling screw channel flow of the fluid.

To aid in describing preferred embodiments of the present invention, reference will be made to the term "bone screw". The term "bone screw" is intended to refer to screws of all types which are presently known or will be devised to be used for internal fixation of fractures of mammalian bone. This includes cortical screws, cancellous screws, ASIF screws and machine screws which are contemplated as being useful in connection with the present invention. The combination with plates, pins, nails and the like used in internal or external fixation are contemplated in combination with this invention.

FIG. 1 is a partially cut away schematic of one embodiment of the bone screw device 10 of this invention. There is the shaft 12 with threads 30 and cutting edge 40. Elevation line 42 shows the height of the kerf or cutting edge 40 above the root 44 reference point. Elevation line 46 illustrates the diameter height of threads 30, in this embodiment. It may be appreciated therefore, that cutting edge 40 forms an excavated zone above root 44 reference location around the device upon insertion into bone. This feature is designed to cut a pathway to allow dispersion of tissue reinforcement material. The height, shape and angle of the cutting edges of this structure control the direction that the material is dispersed. Preferably, this results in the removed material/tissue being directed away from the excavation site and allows for insertion of the reinforcing material in an even distribution to aid in the purchase of the screw in anchoring within weakened bone tissue. Cut away distal portion "A" shows an internal lumen 20 and an optional open tip 50 that communicates with the lumen 20, as shown also in FIG. 17.

FIG. 2 is a partial cutaway view of another embodiment of the invention where an aperture 60 is positioned on the shaft 112 with nearby cutting edge 140 protruding between threads 130 on device 110. The distal portion "A" of the device is a cutaway showing aperture 60 in conjunction with channel 70 which communicates with the lumen 120, and the relative position of the cutting edge 140. This figure also illustrates a closed tip 55 as one embodiment of the invention.

FIG. 3 is a third embodiment of the invention that shows apertures 160 positioned on a middle portion of a shaft 212 without threads. The threads are confined to a distal portion in this embodiment; and the relationship of thread 230 with cutting edge 240 is illustrated with a cutaway portion "A" showing the relationship to lumen 220 and an open tip 150.

FIG. 4 shows a proximal portion of the device with differently sized threads 80, a middle portion of a shaft 312 which is without threads, but with apertures 260, and cutting edges 340. A distal portion of the device comprises threads 330 around shaft 312 with a closed tip 155.

FIG. 5 shows a sleeve 90 designed for insertion in lumen 320 (shown in FIG. 6) inside shaft 412 positioned to block a channel 170 which connects to an aperture 360. FIG. 6 also illustrates the proximate relation of threads 430 and cuttings edges 440 with a closed tip 255. Also in this figure is a truncated enlargement of the sleeve 90 showing a lumen 95 throughout the sleeve for delivery of fluid material through the lumen, channels, and apertures and into the region around the device which was evacuated or created by action of the cutting edges.

FIG. 7 is a schematic view of a body portion 501 comprising a bone 504 having a plurality of zones 1, 2, and 3 adjacent to tension and compression trabeculae 510, 511 representative of such zones and trabeculae in certain body portions. When bone damage occurs through trauma or degenerative processes, the strength of these trabeculae is compromised. It is therefore quite important to reinforce those natural strengthening members through proper placement and selective fixation of any bone screw utilized for repair or strengthening. FIG. 8 shows bone screw 512 and bone reinforcing material placed across each of the main trabeculae and at the triangulated intersection region 517. This placement of bone screw 512 is enhanced by deployment of bone reinforcing material which is dispersed away from the outer surface of the screw and at an angle directionally distally and proximally, from the distal and proximal portions of the screw respectively. The structure and methodology which enables this dispersion pattern not only fills bone voids more effectively, but also prevents migration of the screw by directly locking the screw mechanically and by use of distal and proximal anchoring blocks 522, 523 of set material. This feature is accomplished by using either angled apertures or deflecting the flow from the threads or other features of the screw. This improved purchase of the screw in the bone by proper placement of the screw and use of proximally and distally directed flow of bone reinforcing or strengthening material enables improved outcomes for the patient by truly strengthening at the natural locations for strengthening members and by preventing migration of the screw. These phenomena occur virtually simultaneously with dispersion of the material.

FIGS. 9-11 show the use of movable sleeve 528 used within screw 512 to enable controlled directional dispersal of bone reinforcing material 533 through channels or via 535, 537 in the walls of the sleeve and the screw. As shown, one advantageous pattern of dispersal includes distally oriented flow from the distal end at about a 30° to about a 60° angle α. Further use of such a dispersal pattern in the proximal direction from the proximal portion of the screw, shown in FIG. 11, provides further strengthening function. In one embodiment, angle α is preferably about 45°. A radially oriented dispersal of material may also be helpful from the medial portion of the screw, as shown in FIG. 10. FIGS. 12-16 further illustrate embodiments of these structures which enable the advantages of this invention. It is recognized various combinations of the features disclosed may be utilized to achieve the advantages of the embodiments of this invention.

What is claimed is:

1. A bone screw for entering an area of a host's bone matrix to mechanically strengthen the matrix and radially deliver tissue reinforcement material, the bone screw comprising:
    a shaft comprising a first external threaded portion, a distal end, a middle portion, a proximal end, a circumferential outer shaft wall, and a longitudinal axis extending from the distal end of the shaft to the proximal end of the shaft;
    a lumen defined by the outer shaft wall and extending from the proximal end of the shaft toward the distal end of the shaft;
    at least one directional channel extending through the outer shaft wall from said lumen to at least one aperture on an outer surface of the shaft to deliver tissue reinforcement material from the bone screw; and
    a sleeve comprising a closed distal end and sized to be slideably positionable inside said lumen to selectively block at least one of the channels during delivery of tissue reinforcement material;

wherein the proximal end of the shaft and the lumen are configured to receive at least a portion of the sleeve.

2. The bone screw of claim 1 wherein the first threaded portion of the shaft extends from the proximal end to the distal end.

3. The bone screw of claim 1 wherein the middle portion of the shaft is not threaded.

4. The bone screw of claim 1 wherein the distal end of the shaft has a closed tip.

5. The bone screw of claim 1 wherein at least one aperture is located within a threaded portion of said shaft.

6. The bone screw of claim 5 wherein at least one aperture is located in a grooved section of a threaded portion.

7. The bone screw of claim 6 wherein at least one aperture is located in a land of a threaded portion.

8. The bone screw of claim 1 wherein at least one directional channel is directed proximally at a proximal portion of said screw.

9. The bone screw of claim 1, wherein the shaft further comprises a non-threaded portion, and wherein the diameter of the non-threaded portion is at least equal to the outside diameter of the threaded portion.

10. The bone screw of claim 1, wherein the shaft further comprises a non-threaded portion, and wherein the diameter of the non-threaded portion is less than the outside diameter of the threaded portion.

11. The bone screw of claim 1 wherein at least one aperture is located at a medial portion of the screw and is shaped for directional radial dispersal of a bone reinforcing material therefrom.

12. The bone screw of claim 1, wherein the at least one directional channel is angled towar the distal end of the shaft.

13. The bone screw of claim 1, wherein the sleeve further comprises a central lumen extending along a longitudinal axis of the sleeve, and at least one fluid dispersement channel extending from the lumen of the sleeve to an aperture on an outer wall of the sleeve.

14. The bone screw of claim 1, wherein the distal end of the shaft comprises an open tip in fluid communication with said lumen.

15. The bone screw of claim 14, wherein the sleeve is further sized to block the open tip of the shaft.

16. The bone screw of claim 1, wherein at least one aperture is directed toward the distal end of the shaft.

17. The bone screw of claim 1, wherein the sleeve further comprises a lumen extending along at least a portion of its length and at least one fluid-dispersement channel extending from the lumen to an aperture on an outer tubular wall of the sleeve.

18. A method of fixating a bone screw comprising:

inserting a bone screw into a host's damaged bone matrix so as to cross trabeculae and adjacent zones, wherein the bone screw comprises a distal end, a proximal end, a longitudinal axis extending from the distal end to the proximal end, a lumen extending through the bone screw along the longitudinal axis from the distal end to the proximal end, and at least one directional channel extending from the lumen to at least one aperture on an outer surface of the screw to direct fluid from the lumen at an angle that is generally perpendicular to the longitudinal axis;

inserting a tubular sleeve at least partially into the lumen at the proximal end of the screw, wherein the sleeve comprises a longitudinal axis, an open proximal end, a closed distal end, a lumen extending along at least a portion of a length of the sleeve, and at least one fluid dispersement channel extending from the lumen of the sleeve to an aperture on an outer wall of the sleeve;

connecting a fluid supply to the proximal end of said screw;

supplying fluid into the lumen of the screw through the fluid dispersement channel of the sleeve for distributing the fluid through at least one of the apertures of the screw; and sliding the sleeve within the lumen of the screw along the longitudinal axis of the screw to a position that blocks fluid from flowing into at least one of the directional channels of the screw.

19. The method of claim 18 wherein the fluid is selected from the group of recombinant bone growth factors, hydroxyapatite, and calcium phosphate.

20. A bone screw for mechanically strengthening the matrix of a bone and directionally and selectively delivering tissue reinforcement material, the bone screw comprising:

a shaft comprising a first external threaded portion, a distal end, a middle portion, a proximal end, a circumferential outer shaft wall, and a longitudinal axis extending from the distal end of the shaft to the proximal end of the shaft;

a lumen defined by the outer shaft wall and extending from the proximal end of the shaft toward the distal end of the shaft;

an opening through the outer shaft wall that allows for fluid flow from the distal end of the shaft in a direction that is generally perpendicular to the longitudinal axis of the bone screw;

at least one directional non-radial channel extending through the outer shaft wall from said lumen to at least one aperture on an outer surface of the shaft to deliver tissue reinforcement material from the device; and a tubular sleeve having a proximal end, a closed distal end, and a central channel extending through the entire length of the sleeve from the proximal end to the distal end, wherein the sleeve is positionable and slideable inside the lumen of the shaft to selectively allow fluid movement from the distal end of the sleeve to at least one directional channel of the shaft.

* * * * *

UNITED STATES PATENT AND TRADEMARK OFFICE
CERTIFICATE OF CORRECTION

PATENT NO. : 7,608,097 B2  Page 1 of 1
APPLICATION NO. : 10/836006
DATED : October 27, 2009
INVENTOR(S) : Richard F. Kyle It is certified that error appears in the above-identified patent and that said Letters Patent is hereby corrected as shown below:

Column 5,
Claim 12, Line 34, please delete "towar" and insert in place thereof, --toward--.

Signed and Sealed this

Eighth Day of December, 2009

David J. Kappos
*Director of the United States Patent and Trademark Office*